(12) United States Patent
Ferguson et al.

(10) Patent No.: US 7,566,446 B2
(45) Date of Patent: Jul. 28, 2009

(54) WOUND HEALING AND TREATMENT OF FIBROSIS

(75) Inventors: Mark W. J. Ferguson, Derbyshire (GB); Sharon O'Kane, Derbyshire (GB)

(73) Assignee: Renovo Limited, Manchester (GB)

( * ) Notice: Subject to any disclaimer, the term of this patent is extended or adjusted under 35 U.S.C. 154(b) by 0 days.

(21) Appl. No.: 11/540,956

(22) Filed: Oct. 2, 2006

(65) Prior Publication Data

US 2007/0087969 A1    Apr. 19, 2007

Related U.S. Application Data

(63) Continuation of application No. 09/962,604, filed on Sep. 26, 2001, now abandoned, which is a continuation of application No. 09/319,227, filed as application No. PCT/GB97/03243 on Dec. 4, 1997, now abandoned.

(60) Provisional application No. 60/032,115, filed on Dec. 5, 1996.

(30) Foreign Application Priority Data

Dec. 4, 1996    (GB) .................................. 9625148.3

(51) Int. Cl.
  *A61K 31/74* (2006.01)
  *A01N 37/18* (2006.01)
  *C07K 14/00* (2006.01)

(52) U.S. Cl. .......................... 424/78.06; 514/2; 530/350

(58) Field of Classification Search ........................ None
  See application file for complete search history.

(56) References Cited

U.S. PATENT DOCUMENTS

| | | | |
|---|---|---|---|
| 4,950,483 | A | 8/1990 | Ksander et al. |
| 5,242,902 | A | 9/1993 | Murphy et al. |
| 6,331,298 | B1 | 12/2001 | Ferguson et al. |
| 6,387,364 | B1 | 5/2002 | Ferguson |

FOREIGN PATENT DOCUMENTS

| | | |
|---|---|---|
| EP | 0 261 599 | 3/1988 |
| EP | 0 280 560 | 8/1988 |
| WO | WO 91/15770 | 10/1991 |
| WO | WO 93/04164 | 3/1993 |
| WO | WO 93/19769 | 10/1993 |
| WO | WO 94 22465 A | 10/1994 |

OTHER PUBLICATIONS

Cunningham et al (Science 251: 1233-1236, 1991).*
Looi (Malaysian J. Path. 17(1): 1-10, 1995).*
Erlich et al (J. Cell. Phys. 182: 303-309, 2000).*
Mace et al (J. Cell Sci. 118: 2567-2577, 2005).*
Rudinger (In Peptide Hormones J.A. Parsons, Ed. University Park Press, Baltimore, 1976, pp. 1, 6, and 7).*
Ngo et al (In The Protein Folding Problem and Tertiary Structure Prediction, K. Merz Jr. and S. Legrand, Eds. Birkhauser, Boston, 1994, pp. 433 and 492-495.)*
Kubler W et al: "Changes in the Distribution of Actin-Associated Proteins During Epidermal Wound Healing." J Invest Dermatol 100 )6). 1993 785-789.
Witke W et al: Hemostatic, Inflammatory, and Fibroblast Responses Are Blunted in Mice Lacking Gelsolin.: Cell 81 (1). 1995. 41-51.
Vasconcellos et al, "Reduction is viscosity of cystic fibrosis sputum in vitro by gelsolin", Science 263:969-971 (1994).
Shiels et al, "Actin filaments mediate DNA fiber formation in chronic inflammatory airway disease", American Journal of Pathology 148(3):919-927 (1996).
Rodriques et al, "Gelsolin immunoreactivity in corneal amyloid, wound healing, and macular and granular dystrophies", American Journal of Opthalmology 115:644-652 (1993).
Anderson, "Human gene therapy", Nature 392:25-30 (1998).
Crystal, Science 270:404-410 (1995).
Verma et al, Nature 389:239-242 (1997).
Eck et al, Goodman & Gillman's The Pharmacological Basis of Therapeutics, 9th Ed. Chapter 8 McGraw-Hill, pp. 77-101 (1995).
Nakajima et al, "Expression of Smooth Muscle Alpha-Actin in Mesenchymal Cells During Formation of Avian Endocardial Cushion Tissue: A Role for Transforming Growth Factor β3", Developmental Dynamics 209:296-309 (1997).
Fishkind and Wang, "Orientation and Three-dimensional Organization of Actin Filaments in Dividing Cultured Cells", The Journal of Cell Biology 123(4):837-848 (1993).
Downey et al, "Phorbol Ester-Induced Actin Assembly in Neutrophils: Role of Protein Kinase C", The Journal of Cell Biology 116(3):695-706 (1992).
Coluccio and Tilney, "Phalloidin Enhances Actin Assembly by Preventing Monomer Dissociation", The Journal of Cell Biology 99:529-535 (1984).
Hartwig et al, "Marcks is an actin filament crosslinking protein regulated by protein kinase C and calcium- calmodulin", Nature 356:618-622 (1992).
Xu et al, "Differing Structural Requirements for GTPase-activating Protein Responsiveness an NADPH Oxidase Activation by Rac", The Journal of Biological Chemistry 269(38):23569-23574 (1994).
Rudlinger, "Characteristics of the amino acids as components of a peptide hormone sequence", Peptide Hormones, edited by J.A. Parsons, University Park Press, Baltimore (1976), pp. 1, 6, and 7).
Ngo et al, "Computational Complexity, Protein Structure Prediction, and the Levinthal Paradox", The Protein Folding Problem and Tertiary Structure Prediction, K. Merz Jr. and S. LeGrand, Eds., Birkhauser, Boston (1994), p. 433&492-495.

(Continued)

*Primary Examiner*—Richard Schnizer
(74) *Attorney, Agent, or Firm*—Nixon & Vanderhye P.C.

(57) ABSTRACT

Compositions for use in the treatment of wounds and fibrosis comprising a therapeutically effective amount of a compound that modulates actin assembly and organization intracellularly and/or extracellularly and a pharmaceutically acceptable vehicle; such a compound promotes the rate of wound healing and also prevents or reduces fibrosis. A preferred compound is gelsolin.

5 Claims, 3 Drawing Sheets

OTHER PUBLICATIONS

Yin and Stossel, "Purification and Structural Properties of Gelsolin, A Ca2+-activated Regulatory Protein of Macrophages", The Journal of Biological Chemistry 255(19):9490-9493 (1980).

Hubchak et al, "Cytoskeletal Rearrangement and Signal Transduction in TGF-β1-Stimulated Mesangial Cell Collagen Accumulation", J. Am. Soc. Nephrol. 14:1969-1980 (2003).

Coomber, Brenda L., "Cytoskeleton in TGF-β- and bFGF-Modulated Endothelial Monolayer Repair", Experimental Cell Research 194:42-47 (1991).

Cunningham et al, "Enhanced Motility in NIH 3T3 Fibroblasts That Overexpress Gelsolin", Science 251:1223-1236 (1991).

Looi, Malaysian J. Path. 17(1):1-10 (1995).

Erlich et al, J. Cell. Phys. 182:303-309 (2000).

Mace et al, J. Cell. Sci. 118:2567-2577 (2005).

* cited by examiner

WOUND HEALING AND TREATMENT OF FIBROSIS

This application is a continuation of U.S. application Ser. No. 09/962,604 filed Sep. 26, 2001, now abandoned, which is a continuation of U.S. application Ser. No. 09/319,227 filed Aug. 23, 1999, now abandoned, which is the U.S. national phase of international application PCT/GB97/03243 filed Dec. 4, 1997, which designated the U.S. and which claims priority from GB Application No. 9625148.3 filed Dec. 4, 1996 and claims benefit of U.S. Provisional Application 60/032,115 filed Dec. 5, 1996. The entire contents of these applications are incorporated herein by reference.

The present invention relates to wound healing, and also to regulating fibrosis in the treatment of conditions in which fibrosis is a major mechanism of tissue repair or where excessive fibrosis leads to pathological derangements and malfunctioning of tissue.

Wound healing in adults is a complicated reparative process. The healing process begins with the recruitment of a variety of specialised cells to the site of the wound and involves, extracellular matrix and basement membrane deposition, angiogenesis, selective protease activity and re-epithelialisation. An important component of the healing process in adult mammals is the stimulation of fibroblasts to generate the extracellular matrix. This extracellular matrix constitutes a major component of the connective tissue which develops to repair the wound area.

The connective tissue that forms during the healing process is often fibrous in nature and commonly forms into a connective tissue scar (a process known as fibrosis).

A scar is an abnormal morphological structure resulting from a previous injury or wound (e.g. an incision, excision or trauma). Scars are composed of a connective tissue which is predominately a matrix of collagen types 1 and 3 and fibronectin. The scar may consist of collagen fibres in an abnormal organisation (as seen in scars of the skin) or it may be an abnormal accumulation of connective tissue (as seen in scars of the central nervous system). Most scars consist of abnormally organised collagen and also excess collagen. In man, in the skin, scars may be depressed below the surface or elevated above the surface of the skin. Hypertrophic scars are a more severe form of normal scarring, are elevated above the normal surface of the skin and contain excessive collagen arranged in an abnormal pattern. A keloid is another form of pathological scarring which is not only elevated above the surface of the skin but also extends beyond the boundaries of the original injury. In a keloid there is excessive connective tissue which is organised in an abnormal fashion predominately in whirls of collagenous tissue. There are genetic predispositions to forming both hypertrophic scars and keloids. They are particularly common in Africo-Carribean and Mongoloid races.

There is a need to provide medicaments that promote the healing of wounds. For example, it is often desirable to increase the rate of healing in the case of acute wounds (such as penetrative injuries, burns, nerve damage or even wounds resulting from elective surgery). chronic wounds (such as diabetic, venous and decubitus ulceration) or for generally healing compromised individuals (for example the elderly). In these examples, the wounds can severely influence quality of life or even result in death and therefore the rate of healing often needs to be increased as much as is clinically possible. Where the rate of wound healing is increased, there is often an associated increase in scar formation hut this may be of secondary importance compared to the desired increase in the rate of healing.

The term "wound" as used herein is exemplified but not limited to injuries to the skin. Other types of wound can involve damage, injury or trauma to an internal tissue or organ such as the lung, kidney, heart, gut, tendons or liver.

There are however other instances where the regulation of scar formation is of primary importance and the rate of wound healing is only of secondary consideration. Examples of such situations are scars of the skin where excessive scarring may be detrimental to tissue function and particularly when scar contracture occurs (for instance skin burns and wounds which impair flexibility of a joint). The reduction of scarring to the skin when cosmetic considerations are important is also highly desirable. In the skin, hypertrophic or keloid scars (particularly in Africo-Caribbean and Mongoloid races) can cause functional and cosmetic impairment and there is a need to prevent their occurrence. Scarring resulting from skin grafts in both donor sites and from the application of artificial skin can also be problematic and need to be minimised or prevented.

As well as scars of the skin, internal scarring or fibrosis can be highly detrimental and specific examples include:

(i) Within the central nervous system, glial scarring can prevent neuronal reconnection (e.g. following neuro-surgery or penetrating injuries of the brain).

(ii) Scarring in the eye can be detrimental, in the cornea, scarring can result in abnormal opacity and lead to problems with vision or even blindness. In the retina, scarring can cause buckling or retinal detachment and consequently blindness. Scarring following wound healing in operations to relieve pressure in glaucoma (e.g. glaucoma filtration surgery results in the failure of the surgery whereby the aqueous humour fails to drain and hence the glaucoma returns.

(iii) Scarring in the heart (e.g. following surgery or myocardial infarction) can give rise to abnormal cardiac function.

(iv) Operations involving the abdomen or pelvis, often result in adhesion between viscera. For instance, adhesions between elements of the gut and the body wall may form and cause twisting in the bowel loop leading to ischaemia, gangrene and the necessity for emergency treatment (untreated they may even be fatal). Likewise, trauma or incisions to the guts can lead to scarring and scar contracture to structures which cause occlusion of the lumen of the guts which again can be life threatening.

(v) Scarring in the pelvis in the region of the fallopian tubes can lead to infertility.

(vi) Scarring following injury to muscles can result in abnormal contraction and hence poor muscular function.

(vii) Scarring or fibrosis following injury to tendons and ligaments can result in serious loss of function.

Related to the above is the fact that there are a number of medical conditions known as fibrotic disorders in which excessive fibrosis leads to pathological derangement and malfunctioning of tissue. Fibrotic disorders are characterised by the accumulation of fibrous tissue (predominately collagens) in an abnormal fashion within the tissue. Accumulation of such fibrous tissues may result from a variety of disease processes. These diseases do not necessarily have to be caused by surgery, traumatic injury or wounding. Fibrotic disorders are usually chronic. Examples of fibrotic disorders include cirrhosis or the liver, liver fibrosis, glomerulonephritis, pulmonary fibrosis, scleroderma, myocardial fibrosis, fibrosis following myocardial infarction, central nervous system fibrosis following a stroke or neuro-degenerative disorders (e.g. Alzheimer's Disease, proliferative vitreoretinopathy (PVR) and arthritis. There is therefore also a need for medicaments which may be used for the treatment of such conditions by regulating (i.e. preventing, inhibiting or reversing) fibrosis/scarring in these fibrotic disorders.

Whilst the above considerations mainly apply to conditions, disorders or diseases of man it will be appreciated that wound healing, scarring and fibrotic disorders can also be problematic in other animals, particularly veterinary or domestic animals (e.g. horses, cattle, dogs, cats etc). For instance abdominal wounds or adhesions are a major reason for having to put down horses (particularly race horses), as are tendon and ligament damage leading to scarring or fibrosis.

There have been several recent developments in the fields of wound healing, scarring and fibrotic disorders. Some of these developments revolve around the recent understanding that an array of cytokines and growth factors are intimately involved in the repair of tissues.

WO-A-92/17206 discloses the use of neutralising agents for fibrosis promoting growth factors that may be used to inhibit scar formation during wound healing. For instance, WO-A-92/17206 demonstrates that compositions which specifically inhibit the activity of Transforming Growth Factors β1 and β2 and Platelet Derived Growth Factor are particularly beneficial for reducing scar formation.

WO-A-93/19769 discloses the use of non-fibrotic growth factors, such as Transforming Growth Factors β3 which was surprisingly found to promote healing of a wound without inducing fibrosis.

GB-A-2,288,118 discloses the use of specific antibodies generated against growth factors that improve healing by potentiating the actions of said growth factors.

Another development involves the use of mannose-6-phosphate for use in treating fibrotic disorders associated with accumulation of extracellular matrix and with elevated levels of Transforming Growth Factors β1 or β2 (GB-A-2,265,310). Mannose-6-phosphate is believed to interfere with the conversion of latent forms of these Transforming Growth Factors into their active form.

Other compositions that influence growth factor efficacy and promote wound healing are disclosed in WO-A-95/26203.

Despite such advances there remains a need to continue to develop medicaments that may be used to modulate the healing of wounds, scarring and fibrosis. In particular there is a need for medicaments which do not compromise the rate of wound healing or quality of scar in favour of one or the other.

As discussed more fully below, the invention relates in its broadest aspect to the use of compounds that modulate actin assembly and organisation for the treatment of wounds.

All eukaryotic cells, whether simple unicellular organisms or cells from human tissue, contain actin. Actin may be found as filamentous actin (F actin) which is a major protein component of the cytoskeleton of the cell. The cytoskeleton influences many cellular functions and is particularly relevant in the regulation of motility, shape changes, chemotaxis and secretion.

F actin is a polymer comprised of a tight helix of uniformly orientated actin monomers. These monomers are expressed in the cell as single polypeptide globular proteins known as globular actin (G actin). Polymerisation of G actin monomers into F actin occurs within the cytoplasm of the cell.

F actin is a dynamic structure and the size of the filament may be regulated, according to the functional needs of the cell. For instance, by altering the rate at which G actin monomers are added or removed from the filament or by inhibiting or promoting F actin degradation. As well as forming part of the cytoskeleton, F actin may also be organised into cellular structures, such as thin filaments in muscle, each of which may have a specific cellular function.

Many regulatory proteins influence F actin assembly and organisation. One such class of these regulatory proteins are those which bind to actin monomers, cap the fast growing end of actin filaments and sever actin filaments. Examples of this class of regulatory proteins include gelsolin, villin, CapG, adseverin, flightless-1 and advillin.

Gelsolin is an 82 kDA protein found naturally in cells such as platelets, fibroblasts, neutrophils and macrophages and can shear in half a 1 μm actin filament in only one second. An academic paper by Witke et al. (Cell vol. 81 p 41-51, 1995) has established using a mouse model which had been engineered so as not to express gelsolin (also known as a Gsn mouse of gelsolin knockout mouse) that the motility of neutrophils and fibroblasts is impaired in vitro and in vivo in cells that do not express gelsolin.

This paper does not contemplate the use of gelsolin and similar compounds for the treatment of wounds and surprisingly the inventors have established that compounds which modulate actin assembly and organisation are useful for wound healing.

According to a first aspect of the present invention there is provided the use of a compound that modulates actin assembly and organisation intracellularly and/or extracellularly for the manufacture of a medicament for the treatment of wound or fibrosis.

According to a second aspect of the present invention, there is provided a composition comprising a therapeutically effective amount of a compound that modulates actin assembly and organisation intracellularly and/or extracellularly and a pharmaceutically acceptable vehicle for the treatment of wounds or fibrosis.

According to a third aspect of the present invention, there is provided a method of treating wounds or fibrosis comprising applying to the affected tissue a therapeutically effective amount of a compound which modulates actin assembly and organisation intracellularly and/or extracellularly.

In accordance with the invention, the inventors have established that compounds which modulate actin assembly and organisation may be used to treat wounds to improve the quality of scar formed and also to improve the rate of healing of wounds. The compounds may also be used to treat conditions in which there is inappropriate fibrosis.

The compounds are effective for modulating assembly and organisation of intracellular actin and/or extracellular located actin (which may be released from dead or damaged cells for instance).

Compounds which modulate actin assembly and organisation may be used according to the invention in situations or conditions where scarring needs to be prevented or reduced such as:

(i) where scars of the skin may be excessive and/or detrimental to tissue function and particularly when scar contracture occurs or may occur (for instance skin burns and wounds which impair flexibility of a joint and particularly scarring in children);

(ii) scarring to the skin when cosmetic considerations are important;

(iii) when hypertrophic or keloid scars (particularly in Africo-Caribbean and Mongoloid races) may occur which can cause functional and cosmetic impairment;

(iv) scarring resulting from skin grafts in both donor sites and from the application of artificial skin;

(v) scarring within the central nervous system (e.g. following neuro-surgery or penetrating injuries of the brain), for example, glial scarring can prevent reconnection of severed neurons;

(vi) scarring in the eye and particularly of the cornea (scarring can result in abnormal opacity and lead to problems with vision or even blindness), in the retina (scarring can cause buckling or retinal detachment and consequently blindness) and scarring following wound healing in operations to relieve pressure in glaucoma (e.g. glaucoma filtration surgery which can result in the failure of the surgery whereby the aqueous humour fails to drain and hence the glaucoma returns;

(vii) scarring in the heart (e.g. following surgery or myocardial infarction) which can give rise to abnormal cardiac function;

(viii) scarring of the gut such as may occur following operations involving the abdomen or pelvis that result in adhesion between viscera (adhesions between elements of the gut and the body wall can form and cause twisting in the bowel loop leading to ischaemia, gangrene and the necessity for emergency treatment—untreated they may even be fatal): likewise, trauma or incisions to the guts can lead to scarring and scar contracture or strictures which cause occlusion of the lumen of the guts which again can be life threatening;

(ix) scarring in the pelvis in the region of the fallopian tubes which can lead to infertility;

(x) scarring following injury to muscles which can result in abnormal contraction and hence poor muscular function;

(xi) scarring or fibrosis following injury to tendons and ligaments which can result in serious loss of function.

The compounds may also be used for the treatment or prevention of fibrosis. For instance the compounds may be used to treat fibrotic disorders such as cirrhosis of the liver, liver fibrosis, glomerulonephritis, pulmonary fibrosis, scleroderma, myocardial hibernation, fibrosis following myocardial infarction, central nervous system fibrosis following a stroke or neuro-degenerative disorders (e.g. Alzheimer's Disease), proliferative vitreoretinopathy (PVR) and arthritis.

The compounds are useful for reducing or preventing fibrosis in fibrotic diseases and for reducing or preventing the formation of fibrosis that manifests as hypertrophic scarring or keloids (particularly of the skin).

Compounds which modulate actin assembly and organisation also increase the rate of healing as well as improving scar quality or treating fibrosis. We have found that these compounds are capable of accelerating the rate at which a wound heals. Thus such compounds will be useful for acute wounds (such as penetrative injuries, burns, nerve damage, damaged ligaments or tendons, or even wounds resulting from elective surgery), chronic wounds (such as diabetic, venous, decubitus ulceration and pressure sores) or for generally healing compromised individuals (for example the elderly). The compounds are particularly useful for treating wounds of the skin (i.e. dermal wounds). The abovedescribed wounds can severely influence quality of life or even result in death and therefore the rate of healing may need to be increased as much as is clinically possible.

A most preferred compound for use according to the invention is gelsolin.

The inventors have performed studies which demonstrate that compounds which modulate actin assembly and organisation influence wound healing. For instance, they have found that wound healing is impaired and scar quality reduced in a Gelsolin Knockout Mouse model. Furthermore addition of compounds such as gelsolin from an exogenous source improves scar quality and the rate of wound healing compared to healing observed for untreated wounds.

Further to the Witke et al. paper the inventors have surprisingly found that compounds which modulate actin assembly and organisation are particularly effective for treating wounds to reduce scar formation and also to increase the rate of wound healing. Although the applicants do not wish to be constrained by any hypothesis they believe that the compounds, such as the regulatory protein gelsolin, are effective for reducing scarring because they have found that not only do these compounds modulate the motility of cells but they also influence mobility of the cells within a wound, effect secretion of components of the extracellular matrix and thereby regulate fibrosis and scar formation. The inventors believe these functions are regulated by remodelling F actin within and without these cells. Furthermore the inventors believe that the compounds effect fibroblast orientation within the wound. The orientation of the fibroblasts also influences the nature, organisation and orientation of the extracellular matrix deposited by the fibroblasts and therefore influences the connective tissue scar which repairs the wounded area. The inventors have found that collagen deposition within the matrix is particularly influenced by the compounds. The inventors have also demonstrated that soluble, extracellular gelsolin binds to and clears extracellular actin released from degenerating cells at the wound site and that this clearance of cellular debris may be an important mechanism in accelerating the healing of chronic wounds. The inventors therefore believe that the application to a wound of compounds used according to the invention improves the final quality and appearance of the scar and increases the rate of wound healing as described above.

Whilst gelsolin is the preferred compound other compounds such as villin, CapG, adseverin, flightless-1 and advillin or derivatives thereof may also be used according to the invention.

Compounds used according to the invention may be proteins. Such proteins can easily be modified (for instance by amino acid addition, substitution or deletion) to form derivatives which retain the ability to bind to actin monomers, cap the fast growing end of actin filaments or sever actin filaments. Therefore derivatives which retain functional characteristics of naturally occurring proteins are also preferred compounds of the invention. Examples of such derivatives include functionally active fragments of naturally occurring proteins and even precursors of naturally occurring proteins (e.g. proproteins) which are activated in situ.

Wound healing compositions used according to the invention may take a number of different forms depending, in particular on the manner in which they are to be used. Thus, for example, they may be in the form of a liquid, ointment, cream, gel, hydrogel, powder or aerosol. All of such compositions are suitable for topical application to skin which is a preferred means of administering compounds of the invention to a subject (person or animal) in need of treatment.

The composition may be provided on a sterile dressing or patch which may be used to cover or even pack a wound to be treated. Alternatively the composition of the invention may be an injectable solution or provided as eye drops.

It will be appreciated that the vehicle of the composition of the invention should be one which is well tolerated by the patient and allows release of the active compound to the wound. Such a vehicle is preferably biodegradeable, bioresolveable and/or non-inflammatory.

The composition of the invention may be used in a number of ways. Thus, for example, a composition may be applied in, and/or around a wound of a patient to regulate wound healing. If the composition is to be applied to an "existing" wound, then the pharmaceutically acceptable vehicle will be one which is relatively "mild" i.e. a vehicle which is biocompatible, biodegradable, bioresolvable and non-inflammatory.

It is also possible to use compositions in accordance with the invention prior to surgery (particularly elective surgery so as to provide for regulation of healing of the subsequently formed surgical wound. In this case the vehicle of a topically applied composition may need to be one capable of going across the keratinous layer of the skin. Examples of suitable vehicles for the purpose include dimethyl sulphoxide and acetic acid. Such prophylactic use is a preferred use of compounds according to the invention.

The compositions are suitable to be used for accelerating healing and reducing or controlling scarring resulting form surgical operations on the eye (e.g. laser surgery on the cornea). In this case the composition or medicament may be in the form of an eye drop.

The compositions may be used in a range of internal wound healing applications. Thus for example, the composition may be formulated for inhalation for use in wound healing of the lungs or for the prevention or treatment of fibrosis and strictures in the lung.

It will be appreciated that the amount of a compound that modulates actin assembly and organisation to be applied to the wound site depends on a number of factors such as the biological activity and bioavailability of the compound, which in turn depends on the mode of administration and the physicochemical properties of the compound. Other factors include:

A) The half-life of the compound in the subject being treated.
B) The specific condition to be treated.
C) Whether quick healing or reduced scarring is desired.
D) The age of the subject.

The frequency of administration will also be influenced by the above mentioned factors and particularly the half-life of the compound within the subject being treated.

Generally when the compositions are used to treat existing wounds or fibrotic disorders the compound should be administered as soon as the wound has occurred or the disorder has been diagnosed. Therapy with the composition should continue until the wound has healed to a clinicians satisfaction or, in the case of a fibrotic disorder, the risk or cause of abnormal fibrous tissue formation has been removed.

Compositions for promoting the rate of wound healing should be applied to a wound as soon as possible after the wound has formed. For acute wounds and wounds of subjects who are healing competent (e.g. the young) application of the composition will ideally be at the time of wounding, preferably within hours of wounding and no longer than a few days post-wounding. For chronic wounds or wounds in the healing compromised (e.g. the elderly) administration should be as soon as possible.

Compositions which modulate scarring and/or fibrotic disorders should also be applied to a wound as soon as possible after the wound has formed. However scars and fibrosis can develop over days or even weeks. Therefore the subject being treated may well benefit by administration of a compound (such as gelsolin) even if it is administered days or even weeks after the wound occurred or the disorder developed (or was diagnosed).

When used as a prophylactic (e.g. before surgery or when there is a risk of developing a fibrotic disorder) the compositions should be administered as soon as the risk of undesirable fibrosis or a potential for a poor rate of wound healing has been recognised (as may be the case in elderly subjects). For instance, a cream or ointment containing gelsolin may be applied to a site on the skin of subject where elective surgery is to be performed and an increased rate of wound healing is subsequently desired. In this case, the composition may be applied during the preoperative preparation of the subject or it may even be desirable to apply the composition in the hours or days preceding the surgery (depending upon the health status and age of subject as well as the size of the wound to be formed).

Frequency of administration will depend upon the biological half-life of the compound used. Typically a cream or ointment containing a compound should be administered to a target tissue such that the concentration of the compound at the wound site or tissue affected by a fibrotic disorder is maintained at a level suitable for having a therapeutic effect. This may require administration daily or even several times daily.

Known procedures, such as those conventionally employed by the pharmaceutical industry (e.g. in vivo experimentation, clinical trials etc), may be used to establish specific formulations of compositions and precise therapeutic regimes (such as daily doses of the compounds and the frequency of administration).

Generally, compositions in accordance with the invention will contain 50-1000 nM of the compound (e.g. gelsolin), most preferably 100-500 nM.

Purely by way of example a composition containing 100-500 μg/ml of gelsolin is suitable for application to an existing (i.e. "open") wound.

By way of further example, a composition which is to be used preoperatively to prevent scarring occurring or improve the rate of healing of a wound resulting from subsequent surgery may contain 500-1000 nM of gelsolin to have the desired effect on wound healing.

A suitable daily dose of a compound which modulates actin assembly and organisation depend upon the factors discussed above as well as upon the size of the wound, or amount of tissue effected by fibrosis, which is to be treated. Typically the amount of a compound required for the treatment of wounds or fibrotic disorders will be within the range of 1 ng to 100 g of the active compound/24 hours depending upon the size of the wound or extent of fibrosis amongst several other factors.

It will also be appreciated that compounds used according to the invention may be isolated from nature or chemically synthesised. Such compounds need not be proteins or even structurally similar to naturally occurring proteins but nevertheless have the same effects on actin assembly and organisation. These compounds are also preferred compounds for use according to the invention.

Proteins and derivatives thereof which are used as compounds for modulating actin assembly and organisation may be prepared by any convenient method, including peptide ligation and complete protein synthesis. Alternatively they may be purified from natural sources. For instance gelsolin may be isolated from neutrophils, platelets or fibroblasts expressing the protein (e.g. by the methods of Bryan J. Methods in Enzymology vol 215 p 88-99, Academic Press, London 1992).

A preferred manner of preparing protein and derivatives thereof for use in the invention is by expression from a recombinant DNA system.

Recombinant DNA technology provides a convenient means by which sufficient quantities of such proteins and derivatives thereof may be formed for use in the manufacture of medicaments in desirable quantities.

Many known methods of administering compounds to a relevant tissue have the disadvantage that it can be difficult to achieve sustained levels of the active compound at a wound site or site of fibrosis over the course of even a few days because the active agents usually have very short half-lives in vivo. The half-lives of the compounds tend to be short for a number of reasons which include:

(i) Degradation by proteases and the like.

(ii) Clearance by binding proteins (e.g. α2 macroglobulin).

(iii) Binding and inhibition of agent activity by extracellular matrix molecules such as decorin and fibronectin.

Furthermore, compounds for wound healing and/or treatment of scarring/fibrosis need to be administered in a suitable vehicle and are often provided as a composition comprising the compound and the vehicle. As outlined above, such vehicles are preferably non-inflammatory, biocompatible, bioresorbable and must not degrade or inactivate the active compound (in storage or in use). However, it can often be difficult to provide a satisfactory vehicle for delivering specific compounds to a tissue to be treated.

A convenient way in which these problems can be obviated or mitigated is to provide at a wound site (or site of fibrosis) a therapeutically effective, wound healing amount of a compound that modulates actin assembly and organisation by gene therapy.

According to a fourth aspect of the present invention there is provided a delivery system for use in a gene therapy technique, said delivery system comprising a DNA molecule encoding for a protein which modulates actin assembly and organisation, said DNA molecule being capable of being transcribed to lead to the expression of said protein.

According to a fifth aspect or the present invention there is provided the use of a delivery system as defined in the preceding paragraph for use in the manufacture of a medicament for use in the treatment of wounds or fibrosis.

According to a sixth aspect of the present invention there is provided a method of treating a wounds or fibrosis comprising administering to a patient in need of treatment a therapeutically effective amount of a delivery system as defined for the fourth aspect of the invention.

The delivery systems according to the invention are highly suitable for achieving sustained levels of a compound which modulates actin assembly and organisation at a wound site or site of fibrosis over a longer period of time than is possible for most conventional delivery systems. Protein may be continuously expressed from cells at the wound site or site of fibrosis that have been transformed with the DNA molecule of the invention. Therefore, even if the protein has a very short half-life as an agent in vivo, therapeutically effective amounts of the protein may be continuously expressed from the treated tissue.

Furthermore, the delivery system of the invention may be used to provide the DNA molecule (and thereby the protein which is an active therapeutic agent) without the need to conventional pharmaceutical vehicles such as those required in ointments or creams that are contacted with the wound.

The delivery system of the present invention is such that the DNA molecule is capable of being expressed (when the delivery system is administered to a patient) to produce a protein which directly or indirectly has activity for wound healing and/or treatment of fibrosis or scarring by modulating actin assembly and organisation. By "directly" we mean that the product of gene expression per se has the required activity for wound healing and/or regulating fibrosis or scarring. By "indirectly" we mean that the product of gene expression undergoes or mediates (e.g. as an enzyme) at least one further reaction to provide an agent effective for wound healing and/or regulating fibrosis or scarring by modulating actin assembly and organisation.

It is preferred that the DNA molecule codes for gelsolin or a biologically fragment or derivative thereof. The DNA molecule may also code for compounds such as villin, CapG, adseverin, flightless-1 and advillin or derivatives thereof.

Alternatively the DNA molecule may code for a protein which indirectly increases expression of compounds such as gelsolin. For instance, the DNA molecule may code for an enzyme, transcription factor or the like which promote expression of gelsolin.

The DNA molecule may be contained within a suitable vector to form a recombinant vector. The vector may for example be a plasmid, cosmid or phage. Such recombinant vectors are highly useful in the delivery systems of the invention for transforming cells with the DNA molecule.

Recombinant vectors may also include other functional elements. For instance, recombinant vectors may be designed such that the vector will autonomously replicate in the nucleus of the cell. In this case, elements which induce DNA replication may be required in the recombinant vector. Alternatively the recombinant vector may be designed such that the vector and recombinant DNA molecule integrates into the genome of a cell. In this case DNA sequences which favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required.

The DNA molecule may (but not necessarily) be one which becomes incorporated in the DNA of cells of the subject being treated. Undifferentiated cells may be stably transformed leading to the production of genetically modified daughter cells. When this is the case, regulation of expression in the subject may be required e.g. with specific transcription factors, gene activators or more preferably with inducable promoters which transcribe the gene in response to a signal specifically found at a wound site. Alternatively, the delivery system may be designed to favour unstable or transient transformation of differentiated cells in the subject being treated. In this instance, regulation of expression may be less important because expression of the DNA molecule will stop when the transformed cells die or stop expressing the protein (ideally when the wound, fibrosis or scarring has been treated or prevented).

The delivery system may provide the DNA molecule to the subject without it being incorporated in a vector. For instance, the DNA molecule may be incorporated within a liposome or virus particle. Alternatively the "naked" DNA molecule may be inserted into a subject's cells by a suitable means e.g. direct endocytotic uptake.

The DNA molecule may be transferred to the cells of a subject to be treated by transfection, infection, microinjection, cell fusion, protoplast fusion or ballistic bombardment. For example, transfer may be by ballistic transfection with coated gold particles, liposomes containing the DNA molecule, viral vectors (e.g. adenovirus) and means of providing direct DNA uptake (e.g. endocytosis) by application of plasmid DNA directly to the wounded area topically or by injection.

The protein expressed from the DNA molecule may be one which directly or indirectly provides for wound healing reduced scarring, one which provides an increase in the rate of wound healing whilst possibly resulting in increased scar formation or one which serves to regulate (inhibit, prevent or reverse) fibrosis.

It will be appreciated that the delivery system according to the fourth aspect of the invention may be used according to the fifth or sixth aspects of the invention to treat any of the conditions hereinbefore described.

BRIEF DESCRIPTION OF THE DRAWINGS

The present invention will further be described in the following non-limiting Example which refers to the accompanying drawings, in which.

EXAMPLE 1

Figure 1:
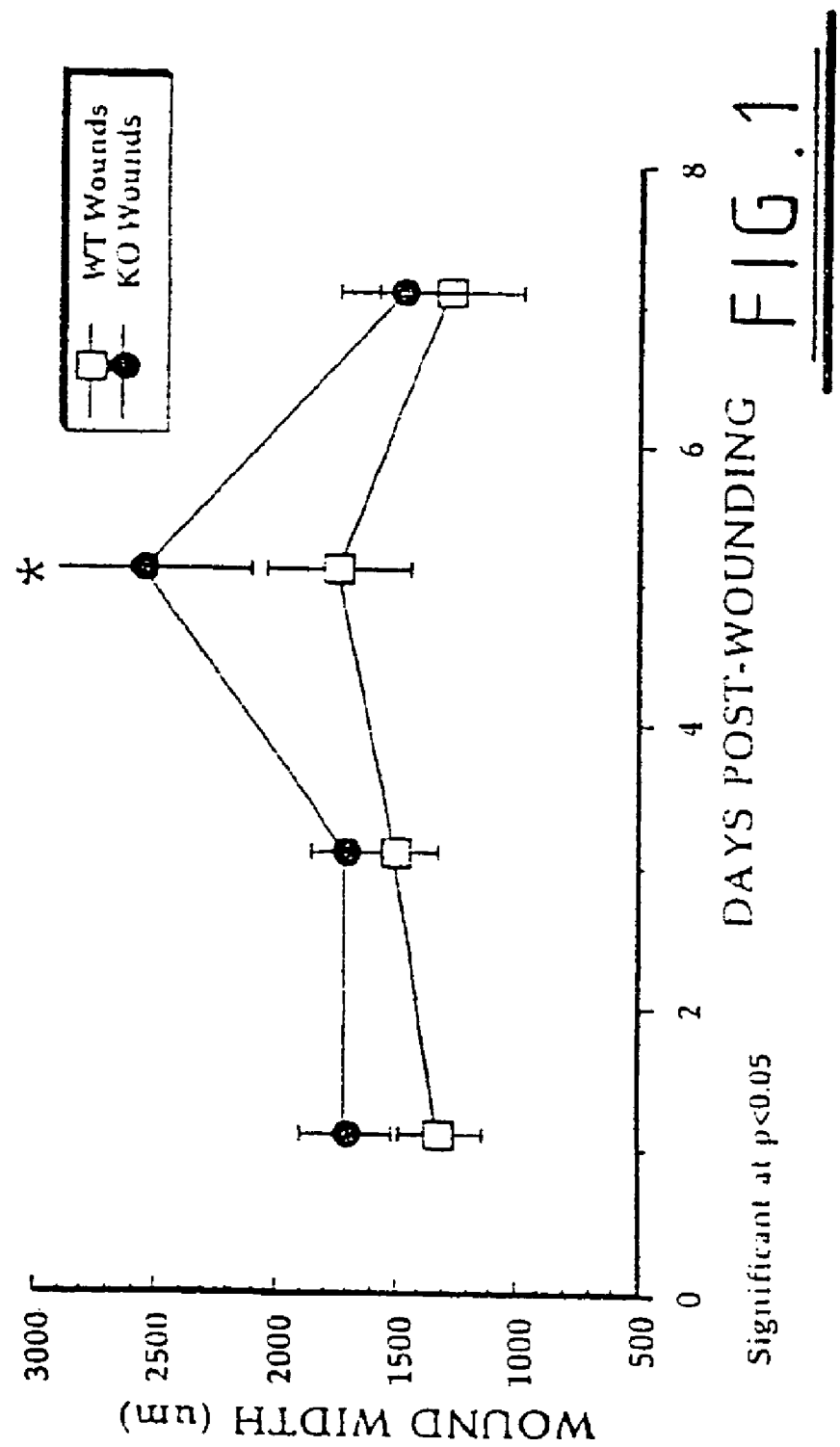
FIG. 1 is a graph of the linear width of wounds in gelsolin knockout and wild type mice from Example 1.

The influence of gelsolin on wound healing was assessed in gelsolin knockout mice (KO—without a gelsolin expression) and normal "wild type" mice (WT—expressing gelsolin). Gelsolin knockout mice generated according to the experimental procedures disclosed in Witke et al. (Cell vol. 81 p 41-51, 1995) were used in the experimental procedures.

1.1 Methods

1.1.1 Treatments 48 adult male mice were divided into six groups of eight: four knockout and four control. The mice were anaesthetised using IP injection of Avertine, the dorsal surface shaved and two 1 cm incisions made through the skin down to and including the panniculus carnosus muscle at specific anatomical positions. The wounds were left unsutured and the animals returned to individual cages. Group of animals were killed after 1 day(d), 3 d, 5 d, 7 d, 14 and 70 d post-wounding and the wounds harvested. Half of each harvested wound was fixed in formal saline and the other half embedded in OCT medium and frozen over liquid nitrogen. Photographic records were kept of the wounds at each time point to enable comparison of microscopic and macroscopic results.

1.1.2 Histological Assessment.

Haematoxylin and Eosin (H&E) and Masson's Trichrome stains were used to determine the cellularity and collagen content of the wounds respectively.

1.1.3 Scoring of Scars 70 Days Post Wounding.

The histology slides were scored using a Visual Analogue Scale (VAS) consisting of a 10 cm line where 0 represents normal skin and 10 a hypertrophic scar/keloid, and separately using a 0-5 rank scale, where 0 represents normal skin and 5 a hypertrophic scar/keloid and 3 is the score for a control scar.

1.1.4 Immunohistochemistry.

The 1, 3, 5 and 7 day wounds were stained using several antibodies including:

1. Anti-mouse fibronectin.
2. Anti-mouse gelsolin, to confirm correct genotyping of gelsolin knockout mice and to determine the immunolocalisation of gelsolin in wild type animal wounds.
3. TRITC-labelled phalloidin. Phalloidin is extracted from the mushroom *amanita phalloides* and binds to filamentous actin (F-actin) so is useful in localising and distinguishing between extra- and intracellular F-actin.

Dual staining with anti-gelsolin (detected with a FITC-labelled secondary antibody) and TRITC phalloidin was carried out to determine whether the extracellular actin observed in the wound co-localised with extracellular gelsolin, since plasma gelsolin released from the blood system may be responsible for clearance of extracellular actin in wounds.

1.1.5 Image Analysis.

Image analysis was carried out using PC based image capture system ('PC Image') and the following parameters were measured in order to quantify differences between knockout and wild type wounds:

1. Wound width (both linear between wound edges and actual perimeter)
2. Retraction of the panniculus carnosus muscle
3. Mid-wound width
4. Re-epithelialisation
5. Scar width at 3 points: base, middle and top
6. Thickness of new epithelium All wounds were measured for wound width and retraction of the panniculus carnosus muscle, the other measurements were taken at appropriate time points.

Statistical analysis of the measurements was performed using the Simfit program written by Dr W Bardsley, University of Manchester. The two statistical tests used were Mann-Whitney U test and the Kolgomorov-Smirnov test to compare results from the wild type control and knockout animals (Table 1).

1.2. Results

1.2.1 Histology.

The most obvious differences between control (WT="wildtype") and knockout mice (KO) were observed at 5 d post-wounding. At 24 h, the knockout mice wounds were similar in appearance to the control wounds; the wounds from all the mice were wide and contained lots of inflammatory cells (see FIG. 1). At 3 d postwounding, the normal wounds were almost re-epithelialised, with the eschars still present and evidence of neovascularisation and collagen formation in the wound area. The wounds of gelsolin knockout mice were very variable in re-epithelialisation, some resembling control wounds, others not re-epithelialised at all. Some of the knockout wounds remained very inflammatory, others not very cellular and in all cases there was a decreased level of new collagen formation.

Figure 2:
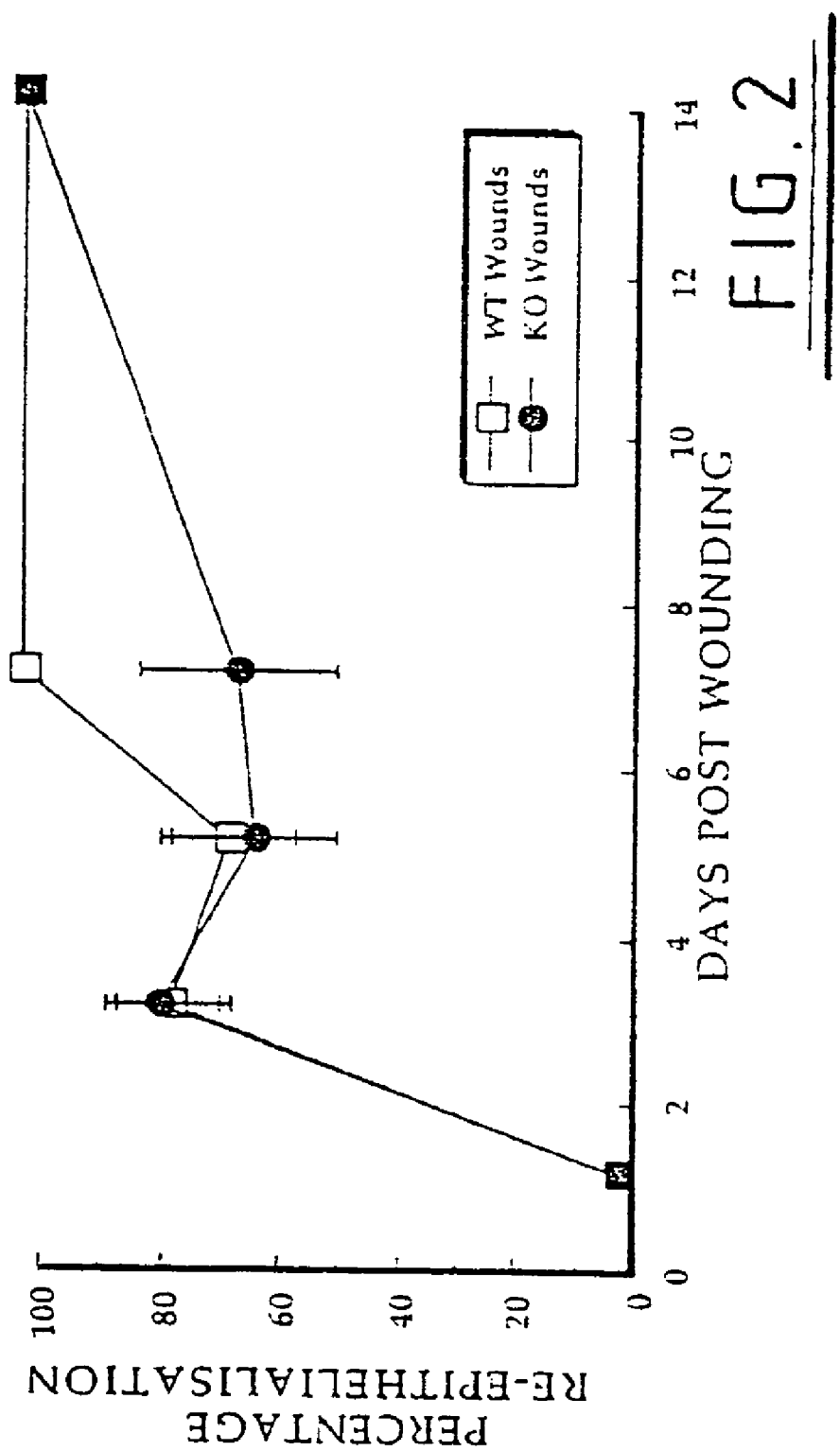
FIG. 2 is a graph of percentage re-epithelialisation of wounds in gelsolin knockout and wild type mice for Example 1.
Figure 3:
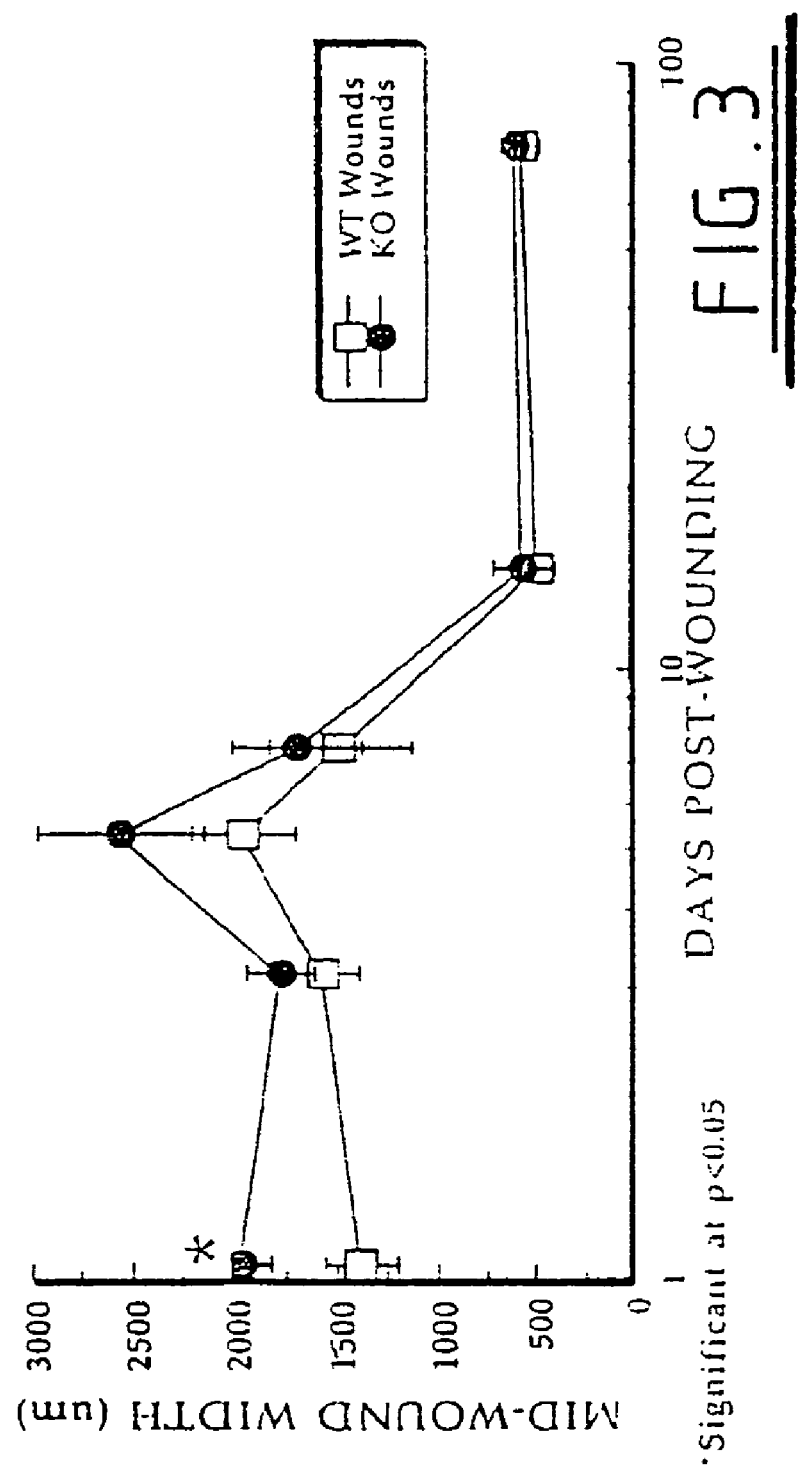
FIG. 3 is a graph of mid-wound/scar width of wounds in gelsolin knockout and wild type mice from Example 1.

At 5 d most of the gelsolin knockout mice wounds remained very wide and had not fully re-epithelialised, in comparison with the wild type controls, where in most cases re-epithelialisation had occurred (FIGS. 2, 3, Table 1). At 7 d the wounds were again heterogeneous, some knockout wounds had re-epithelialised and contained relatively few inflammatory cells, whereas others were still quite wide and cellular and had eschars on the surface. There were clusters of inflammatory cells and fibroblasts within some of the knockout wounds. The control wounds at this stage were mostly re-epithelialised and had high levels of new collagen laid down. The knockout wounds at both 5 and 7 d post-wounding had very low levels of collagen which appeared patchy and was deposited in a marked linear pattern perpendicular to the epithelium. This clustering of cells and patchy collagen arose as a result of normal actin remodelling having been altered in gelsolin knockout mice.

At 14 d, most of the knockout wounds had persistent inflammatory cells and remained quite wide although all had re-epithelialised at this stage. The amount of collagen formed was variable. At 70 d post-wounding the knockout animals had wide scars similar to control animals but there appeared to be a lot of fibroblasts in the knockout scars. Two scars from knockout mice had a striking local accumulation of hair follicles immediately adjacent to and surrounding the scars. In general, the scars from the knockout animals were similar to but of a poorer quality than scars from the wild type animals at this time point.

These results were surprising and show that gelsolin improves the quality of scars (seen after 70 d) and also improves the rate of healing (exemplified by the observations at 5 d). Therefore compounds according to the invention may be used to treat wounds and are particularly useful because they accelerate healing and reduce or prevent scar formation.

TABLE I

Summary of Data from Image Analysis of Gelsolin Knockout and Wild Type Wounds.

Table 1a Wound Width (linear)

| Days Post Wounding | Genotype | Wound Width (μm) (+/− s.e.m.) |
|---|---|---|
| 1 | WT | 1250.01 +/− 171.56 |
| 1 | KO | 1644.82 +/− 188.88 |
| 3 | WT | 1432.5 +/− 185.2 |
| 3 | KO | 1646.5 +/− 145.16 |
| 5 | WT | 1673.55 +/− 299.85* |
| 5 | KO | 2466.98 +/− 430.63* |
| 7 | WT | 1206.74 +/− 302.24 |
| 7 | KO | 1408.01 +/− 265.77 |

*Knockout wounds significantly wider than wild type wounds. Significant at p < 0.05 (Mann-Whitney U Test).

Table 1b Wound Width (perimeter)

| Days Post Wounding | Genotype | Wound Width (μm) (+/− s.e.m.) |
|---|---|---|
| 3 | WT | 1488.54 +/− 171.86 |
| 3 | KO | 1690.63 +/− 173.15 |
| 5 | WT | 2438.48 +/− 357.66 |
| 5 | KO | 3949.5 +/− 945.2 |
| 7 | WT | 1634.14 +/− 404.71 |
| 7 | KO | 2016.41 +/− 425.85 |

Table 1c Panniculus Carnosus Width

| Days Post Wounding | Genotype | Panniculus Width (μm) (+/− s.e.m.) |
|---|---|---|
| 1 | WT | 2175.1 +/− 171.56 |
| 1 | KO | 2740.9 +/− 257.7 |
| 3 | WT | 2408.68 +/− 193.4 |
| 3 | KO | 2578.4 +/− 320.93 |
| 5 | WT | 3383.53 +/− 299.5 |
| 5 | KO | 3948.2 +/− 572.7 |
| 7 | WT | 2617.2 +/− 208.2 |
| 7 | KO | 2620 +/− 217.2 |
| 14 | WT | 1934.7 +/− 151.75 |
| 14 | KO | 2150.0 +/− 214.10 |
| 70 | WT | 3292.5 +/− 312.1* |
| 70 | KO | 2708.9 +/− 173.6 |

*Panniculus carnosus tends to be further retracted in wild type wounds than knockout wounds, p < 0.05 (Mann-Whitney U Test).

Table 1d Mid-Wound Width

| Days Post Wounding | Genotype | Mid-Wound Width (μm) (+/− s.e.m.) |
|---|---|---|
| 1 | WT | 1307.46 +/− 173.76* |
| 1 | KO | 1897.48 +/− 148.2 |
| 3 | WT | 1488.54 +/− 171.86 |
| 3 | KO | 1690.63 +/− 173.15 |
| 5 | WT | 1865.76 +/− 258.02 |
| 5 | KO | 2479.92 +/− 408.56 |
| 7 | WT | 1400.9 +/− 351.45 |
| 7 | KO | 1618.84 +/− 320.31 |

*Knockout wounds significantly wider than wild type wounds. Significant at p < 0.05 (Kolgomorov-Smirnov) and p < 0.01 (Mann-Whitney U Test).

TABLE I-continued

Summary of Data from Image Analysis of Gelsolin Knockout and Wild Type Wounds.

Table 1e Percentage Re-epithelialisation

| Days Post Wounding | Genotype | % Re-epithelialisation (+/− s.e.m.) |
|---|---|---|
| 1 | WT | 0 |
| 1 | KO | 0 |
| 3 | WT | 75.16 +/− 9.6 |
| 3 | KO | 77.07 +/− 9.7 |
| 5 | WT | 70.62 +/− 11.5 |
| 5 | KO | 61.57 +/− 13.7 |
| 7 | WT | 100 |
| 7 | KO | 64.47 +/− 16.7 |
| 14 | WT | 100 |
| 14 | KO | 100 |

Table 1f Mid-Epithelial Thickness (5-14 days only)

| Days Post Wounding | Genotype | Mid-Epithelial thickness (μm) (+/− s.e.m.) |
|---|---|---|
| 5 | WT | 156.82 +/− 78.1 |
| 5 | KO | 494.45 +/− 339.95 |
| 7 | WT | 173.08 +/− 46.5 |
| 7 | KO | 123.15 +/− 37.85 |
| 14 | WT | 50.79 +/− 7.0 |
| 14 | KO | 58.81 +/− 13.0 |

Table 1g Scar Width (14 and 70 days only)

| Days Post Wounding | Genotype | Top | Middle | Base |
|---|---|---|---|---|
| 14 | WT | 412.3 +/− 67.1 | 411.8 +/− 102.1 | 961.1 +/− 150.9 |
| 14 | KO | 593.6 +/− 108.7 | 489.6 +/− 146.9 | 863.4 +/− 208.5 |
| 70 | WT | | 488.9 +/− 103.9 | — |
| 70 | KO | | 530.3 +/− 65.7 | — |

Scar Width (μm) (+/− s.e.m.)

TABLE 2

Scores for 70 Day Scars in Wild Type (WT) and gelsolin Knockout (KO) Animals.

| Slide | Score (VAS) | Score (0-5) |
|---|---|---|
| WT1 | 4.25 | 2 |
| WT2 | 4.35 | 2 |
| WT3 | 4.85 | 3 |
| WT4 | 4.95 | 3 |
| WT5 | 5.25 | 3 |
| WT6 | 6.25 | 4 |
| | Average = 4.0 | Average = 2.25 |
| KO1 | 4.85 | 3 |
| KO2 | 5.6 | 4 |
| KO3 | 5.9 | 4 |
| KO4 | 3.8 | 2 |
| KO5 | 4.25 | 3 |
| KO6 | 5.45 | 3 |
| KO7 | 5.7 | 3 |
| KO8 | 3.45 | 2 |
| | Average = 4.875 | Average = 3 |

1.2.2 Immunocytochemistry.

Dual staining of wound sections from knockout and wild type mice with anti-gelsolin and TRITC-phalloidin was analysed on the Biorad MRC600 confocal microscope to make use of the superior wavelength separation. This prevented any bleed through from the FITC or TRITC into the other channel.

There was no gelsolin present in the knockout wounds, either when stained alone or when dual stained with TRITC-phalloidin. In wild-type wounds at 1 d and 3 d post-wounding, there was a high level of immunostaining for TRITC-phalloidin and this decreased in a temporal manner to 7 days. There was immunostaining of gelsolin in the wild type wounds at all time points analysed which appeared to increase particularly in 7 d wounds, although this may be due to the concomitant decrease in actin labelled with TRITC-phalloidin. There was increasing amounts of immunostaining for TRITC-phalloidin in the gelsolin knockout wounds up to 7 days post-wounding which can be explained by the lack of gelsolin (both cytoplasmic and plasma). This failure of clearance of extracellular actin (released from degenerating cells) in the gelsolin knockout mouse wounds may explain the delayed wound healing, hence addition of exogenous gelsolin may accelerate this clearance and hence accelerate wound healing.

1.2.3 Image Analysis.

The results from the image analysis supported the observation that there were differences in re-epithelialisation of the knockout and wild type wounds and that the most significant differences were between wounds at 5 days post-wounding. See Table 1 and FIG. 2 for summary of results.

1.3 Summary.

1.3.1 Effect on Scarring and/or Fibrosis

The results from this Gelsolin knockout mice wound investigation provide evidence that a lack of gelsolin results in disordered fibroblast orientation in wounds and subsequent poor quality of the resultant scars. This indicates that initial fibroblast orientation is an important factor in determining the final quality of a scar. Therefore compounds that influence actin assembly and organisation, such as gelsolin, are useful for treating wounds and particularly for improving or preventing scar formation.

1.3.2 Effect on the Rate of Wound Healing

The data herein presented for wound width 5 day post-wounding further demonstrates that gelsolin and other compounds that influence actin assembly and organisation are required to increase the rate of wound healing (i.e. reduce the width wound).

1.3.3 General

The results from gelsolin knockout mice provide evidence that prevention of initial wound contraction does not necessarily result in a better scar and may in fact be detrimental, and that delaying wound healing does not improve scarring. The results also indicate that exogenous addition of compounds such as gelsolin which sever or clear extracellular debris, may be useful in accelerating the healing of wounds especially chronic wounds (e.g. venous ulcers, diabetic ulcers or pressure sores).

Furthermore, these data demonstrate that compounds which modulate actin assembly and organisation may be used to treat both aspects of wound healing (i.e. to reduce scarring and at the same time increase the rate of wound healing). This is a surprising effect because most conventional treatments for wounds either reduce scarring or increase the rate of wound healing and very often treatment of one aspect (e.g. scarring) is to the detriment of the other aspect (e.g. rate of healing).

EXAMPLE 2

2.1 Methods

Example 1 was repeated using 11 wild type (WT) and 11 transgenic (KO) littermates. The wound tissue was harvested at 5 days (8 WT and 8 KO) and 7 days (3 WT and 3 KO) post-wounding as these were the time points where significant differences between knockout and control mouse healing were observed in Example 1.

2.2 Results

The analyses of perimeter wound width and re-epithelialisation are summarised in Tables 3 and 4.

2.2.1 Wound Width

Table 3 represents the perimeter width of wounds for Gelsolin null mice (KO) and control mice (WT) at 5 and 7 days post-wounding.

After 5 days, the wounds from KO mice were wider (mean width 2521.7µ) and more cellular than the control wounds (mean width 1310.91µ). Little new collagen was observed and cells were in clusters within the wound area. Statistical analysis (using the Simfit program written by Dr W Bardsley, University of Manchester) demonstrated that the differences between WT and KO mice wound width was highly significant 5 days post-wounding.

Differences in wound width between WT and KO mice after 7 days post-wounding were not significantly different.

2.2.2 Re-epithelialisation

At 5 days post-wounding there was minimal re-epithelialisation (63.4%) in transgenic (KO) compared to wild type (WT) wounds (95.4%) and there were large eschars present. Statistical analysis demonstrated that the differences between WT and KO mice wound width was highly significant 5 days post-wounding.

At 7 days post-wounding, the wounds from Gelsolin null mice (KO) had almost all re-epithelialised (average (re-epithelialisation was 95.03% with only one wound not completely re-epithelialised) and contained some new collagen. The collagen was, however, deposited in a very irregular patchy manner, in a similar fashion to that described in Example 1.

The 7 days post wounding from the control, wild type mice were all re-epithelialised and had high levels of new collagen.

Differences in % re-epithelialisation between WT and KO mice after 7 days post-wounding were not significantly different. However the differences observed in collagen composition were note worthy.

TABLE 3

| Wound Width (perimeter) | | |
|---|---|---|
| Days Post Wounding | Genotype | Wound Width (µm) (+/−s.e.m.) |
| 5 | WT | 1310.91 +/− 856.27* |
| 5 | KO | 2521.675 +/− 970.86* |

TABLE 3-continued

Wound Width (perimeter)

| | | |
|---|---|---|
| 7 | WT | 1634.14 +/− 404.71 |
| 7 | KO | 2016.41 +/− 425.85 |

Statistical Analysis of data in Table 3:

(i) 5 DAYS*

1. Kolgomorov-Smirnov Two Sample Test

H0: F(WT) is equal to G(KO) against:
H1: F(WT) is not equal to G(KO)   p = 0.0007 (Highly significant)
H0 against H3: F(WT) < G(KO)   p = 0.0003 (Highly significant)
2. Mann-Whitney U Test H0: F(WT) is equal to G(KO) against
H1: F)(WT) is not equal to G(KO)   p = 0.0002 (Highly significant)
H0 against H3: F(WT) < G(KO)   p = 0.0001 (Highly significant)

(ii) 7 DAYS

1. Kolgomorov-Smirnov Two Sample Test

H0: F(WT) is equal to G(KO) against
H1: F(WT) is not equal to G(KO)
H0 against H3: F(WT) < G(KO)   p = 0.47 (not significant)
2. Mann-Whitney U Test H0: F(WT) is equal to G(KO) against
H1: F)(WT) is not equal to G(KO)
H0 against H3: F(WT) < G(KO)   p = 0.3 (not significant)

TABLE 4

Percentage Re-epithelialisation

| Days Post Wounding | Genotype | % Re-epithelialisation (+/−s.e.m.) |
|---|---|---|
| 5 | WT | 95.41 +/− 9.25* |
| 5 | KO | 63.43 +/− 24.6* |
| 7 | WT | 100 +/− 0 |
| 7 | KO | 95.0 |

Statistical Analysis of data in Table 3:

(i) 5 DAYS*

1. Kolgomorov-Smirnov Two Sample Test

H0: F(WT) is equal to G(KO) against:
H1: F(WT) is not equal to G(KO)   p = 0.0112 (Highly significant)
H0 against H3: F(WT) < G(KO)   p = 0.0056 (Highly significant)
2. Mann-Whitney U Test H0: F(WT) is equal to G(KO) against
H1: F)(WT) is not equal to G(KO)   p = 0.0012 (Highly significant)
H0 against H3: F(WT) < G(KO)   p = 0.0005 (Highly significant)

(ii) 7 DAYS

1. Kolgomorov-Smirnov Two Sample Test

H0: F(WT) is equal to G(KO) against
H1: F(WT) is not equal to G(KO)
H0 against H3: F(WT) < G(KO)   p = 0.5 (not significant)
2. Mann-Whitney U Test H0: F(WT) is equal to G(KO) against
H1: F)(WT) is not equal to G(KO)
H0 against H3: F(WT) < G(KO)   p = 0.5 (not significant)

To illustrate the significance of the data presented in Examples 1 and 2 the data for both Examples was combined and is presented in tables 5-9.

TABLE 5

Linear Width (μm) of Gelsolin Knockout and Control Mice Wounds.

| Days Post-Wounding | WT (Mean +/− s.e.m) | KO (Mean +/− s.e.m) |
|---|---|---|
| 1 | 1250 +/− 171.6 | 1644.8 +/− 188.9 |
| 3 | 1432.5 +/− 185.2 | 1646.49 +/− 145.16 |
| 5 | 1187.16 +/− 153 | 1910.25 +/− 174.55** |
| 7 | 1022.83 +/− 211.99 | 1353.2 +/− 164.66 |

**p < 0.01

TABLE 6

Retraction Width (μm) of the Panniculus Carnosus Muscle

| Days Post-Wounding | WT (Mean +/− s.e.m) | KO (Mean +/− s.e.m) |
|---|---|---|
| 1 | 2175.11 +/− 176.6 | 2740.89 +/− 257.67 |
| 3 | 2408.68 +/− 193.37 | 2578.36 +/− 320.93 |
| 5 | 2585.22 +/− 172.94 | 3227.3 +/− 207.84* |
| 7 | 2270.18 +/− 199.92 | 2361.12 +/− 166.78 |
| 14 | 1934.70 +/− 151.75 | 2150.03 +/− 214.09 |
| 70 | 3292.50 +/− 312.07 | 2708.94 +/− 173.55 |

*p < 0/05

TABLE 7

Mid-Wound Width (μm)

| Days Post-Wounding | WT (Mean +/− s.e.m) | KO (Mean +/− s.e.m) |
|---|---|---|
| 1 | 1307.46 +/− 173.76 | 1897.48 +/− 148.19 |
| 3 | 1488.54 +/− 171.86 | 1690.63 +/− 173.15 |
| 5 | 1732.64 +/− 144.92 | 2097.28 +/− 173.74* |
| 7 | 1105.52 +/− 245.12 | 1377.49 +/− 202.7 |

*p < 0.05

TABLE 8

Perimeter Wound Width (μm)

| Days Post-Wounding | WT (Mean +/− s.e.m) | KO (Mean +/− s.e.m) |
|---|---|---|
| 3 | 2037.78 +/− 251.11 | 2478.68 +/− 273.66 |
| 5 | 1686.77 +/− 204.23 | 2911.08 +/− 336.18** |
| 7 | 1334.12 +/− 262.29 | 1805.81 +/− 260.48 |

**p < 0.01

TABLE 9

Percentage Re-epithelialisation

| Days Post-Wounding | WT (Mean +/− s.e.m) | KO (Mean +/− s.e.m) |
|---|---|---|
| 3 | 75.16 +/− 9.58 | 77.07 +/− 9.66 |
| 5 | 85.54 +/− 4.73 | 62.92 +/− 5.78** |
| 7 | 100 +/− | 77.57 +/− 10.37 |
| 14 | 100 +/− | 100 +/− |

*p < 0/05.
**p < 0/01

SUMMARY

The results presented in tables 5-9 illustrate that normal actin remodelling in KO mice is inhibited. This affects the process of wound healing in two main ways:

(i) There is a decrease in cell movement (particularly at 5 days post wounding), manifest as decreased keratinocytes and fibroblasts mobility as well as a reduction in re-epithelialisation. We believe this is due to a decrease in intracellular gelsolin in relevant cells.

(ii) There is also a physical barrier to prevent outgrowth of the epithelial cells (and thereby re-epithelialisation due to an accumulation of extracellular actin, which would normally be removed by the action of extracellular gelsolin. This accumulation of extracellular actin also contributes to the poor quality of scar observed in KO mice.

These results and observations demonstrate that wound healing may be improved by administering, to the site of a wound, compounds (such as gelsolin) which modulate actin assembly and organisation. More specifically, re-epithelialisation of wounds is increased by these compounds and therefore the compounds are suitable for increasing the rate of wound healing. Furthermore collagen deposition is more organised in the presence of compounds such as gelsolin and this indicates that compounds used according to the invention are also useful for improving scar quality. These effects are surprising because most conventional treatments for wounds either reduce scarring or increase the rate of wound healing and very often treatment of one aspect (e.g. scarring) is to the detriment of the other aspect (e.g. rate of healing).

It will be appreciated that compounds which modulate actin assembly and organisation are useful for treating fibrosis generally (for example the abovedescribed fibrotic disorders) as well as scarring.

The invention claimed is:

1. A method of reducing scar formation in incisional dermal wounds, the method comprising delivering directly to a dermal wound in need of such treatment a therapeutically effect amount of a regulatory protein that caps the fast growing end of actin filaments and/or severs capped actin filaments so that said scar formation is reduced.

2. The method according to claim 1 wherein the regulatory protein is selected from the group consisting of gelsolin, villin, CapG, adseverin, flightless-1, advillin and amino acid deletion or amino acid addition derivatives thereof.

3. The method according to claim 2 wherein the regulatory protein is gelsolin or an amino acid deletion or amino acid addition derivative thereof.

4. The method according to claim 1 wherein the regulatory protein is selected from the group consisting of gelsolin, villin, CapG, adseverin, flightless-1 and advillin.

5. The method according to claim 4 wherein the regulatory protein is gelsolin.

* * * * *